(12) United States Patent
Himmelreich et al.

(10) Patent No.: US 9,574,225 B2
(45) Date of Patent: Feb. 21, 2017

(54) PREPARATION AND AMPLIFICATION OF NUCLEIC ACIDS BY MEANS OF MAGNETIC PARTICLES

(75) Inventors: Ralf Himmelreich, Langenfeld (DE); Thomas Rothmann, Langenfeld (DE); Roland Fabis, Leverkusen (DE); Christoph Erbacher, Haan (DE)

(73) Assignee: QIAGEN GMBH, Hilden (DE)

( * ) Notice: Subject to any disclaimer, the term of this patent is extended or adjusted under 35 U.S.C. 154(b) by 680 days.

(21) Appl. No.: 13/141,593

(22) PCT Filed: Dec. 23, 2009

(86) PCT No.: PCT/EP2009/067882
§ 371 (c)(1),
(2), (4) Date: Sep. 12, 2011

(87) PCT Pub. No.: WO2010/072822
PCT Pub. Date: Jul. 1, 2010

(65) Prior Publication Data
US 2011/0318784 A1    Dec. 29, 2011

(30) Foreign Application Priority Data

Dec. 23, 2008 (DE) .......... 10 2008 055 120

(51) Int. Cl.
*C12Q 1/68* (2006.01)
*C12N 15/10* (2006.01)
*C07H 21/02* (2006.01)

(52) U.S. Cl.
CPC ....... *C12Q 1/6806* (2013.01); *C12N 15/1013* (2013.01); *C12Q 1/686* (2013.01)

(58) Field of Classification Search
CPC ........ C12Q 2549/119; C12Q 2563/143; C12Q 1/6806; C12Q 1/686; C12Q 2547/101; C12Q 2565/629; C12N 15/1013
See application file for complete search history.

(56) References Cited

U.S. PATENT DOCUMENTS

| | | | | |
|---|---|---|---|---|
| 5,512,439 A | * | 4/1996 | Hornes et al. | 435/6.11 |
| 5,755,942 A | * | 5/1998 | Zanzucchi et al. | 506/32 |
| 6,090,935 A | * | 7/2000 | Breivik et al. | 536/25.4 |
| 2006/0286557 A1 | * | 12/2006 | Basehore et al. | 435/6 |
| 2009/0061450 A1 | * | 3/2009 | Hunter | 435/6 |
| 2009/0071833 A1 | * | 3/2009 | Gorfinkel et al. | 204/601 |

FOREIGN PATENT DOCUMENTS

DE   102005049976 A1   4/2006
EP      1371736 A1   12/2003
(Continued)

OTHER PUBLICATIONS

Banerjee, S.K. et al., Pancreas, vol. 15, pp. 16-24 (1997).*
(Continued)

*Primary Examiner* — Teresa Strzelecka
(74) *Attorney, Agent, or Firm* — Seyfarth Shaw LLP

(57) ABSTRACT

The invention relates to the preparation of a biological sample for performing verifications and examinations, wherein the aim of the invention is the creation of a method for preparing a biological sample having an improved PCR sensitivity compared to the reference standard having standard PCR without having to raise the cost thereof.

13 Claims, 7 Drawing Sheets

(56) References Cited

FOREIGN PATENT DOCUMENTS

| KR | 2002029476 A | | 4/2002 |
|----|----|----|----|
| WO | WO 95/13368 A1 | | 5/1995 |
| WO | WO 2006/121997 | * | 11/2006 |
| WO | WO 2008/147382 A1 | | 12/2008 |

OTHER PUBLICATIONS

Danapure Genomic DNA Extraction Kit , p. 1-3; Oct. 2004); downloaded from www.bioted.es/en/admin/files/pdf/DANAPURE%20%20Plantas%20y%20Hongos.pdf.*
Goode, T. et al., Meth. Mol. Biol., vol. 193, pp. 65-79 (2002).*
Schneider, A. et al., Cancer Res., vol. 60, pp. 4617-4622 (2000).*
Loureiro, J. et al., Ann. Botany, vol. 98, pp. 679-689 (2006).*
Huh, Y.S. et al., Electrophoresis, vol. 28, pp. 4748-4757 (2007).*
Kong, Q. et al., Nucl. Acids Res., vol. 29, e33, pp. 1-5 (2001).*
Smistrup, K. et al., Lab Chip, vol. 5, pp. 1315-1319 (2005).*
Guo, S.S. et al., Microelect. Eng., vol. 83, pp. 1655-1659 (2006).*
Volkheimer, et al., "A single cell analysis of immunoglobulin genes in chronic lymphocytic leukemia (CLL): Progressive somatic mutations in the immunoglobulin heavy and light chains contribute to intraclonal diversification in CLL", Blood, American Society of Hematology, vol. 102, No. 11, Dec. 9, 2003, p. 666A.
Kauppinen, et al., "*Mycobacterium* malmoense—specific nested PCR based on a conserved sequence detected in random amplified polymorphic DNA fingerprints", Journal of Clinical Microbiology, May 1999, vol. 37, No. 5, pp. 1454-1458.
Kim, et al., "Detection of hepatitis a virus from oyster by nested PCR using efficient extraction and concentration method", Journal of Microbiology, vol. 48, No. 4, Aug. 2008, pp. 436-440.

\* cited by examiner

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 1
atgctacccc tgaaaaactc                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcttgaact gatttcctc                                               19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgatgatgct acccctgaaa aact                                         24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tattgtcgct tgaactgatt tcctc                                        25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(1)
<223> OTHER INFORMATION: 6-Fam-c
<220> FEATURE:
<221> NAME/KEY: modified_base
<222> LOCATION: (25)..(25)
<223> OTHER INFORMATION: g-BHQ1

<400> SEQUENCE: 5
cgttgttaag tcaatggaaa acctg                                        25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caccaaaaga gaactgcaat g                                            21

<210> SEQ ID NO 7
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggagcgaccc agaaagttac cac                                            23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggattcccat ctctatatac ta                                             22

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcataaatcc cgaaaagcaa agtca                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (25)..(25)
<223> OTHER INFORMATION: g-BHQ-FAM

<400> SEQUENCE: 10
agaatgtgtg tactgcaagc aacag                                          25

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgaagttt accaatcaat                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tatttatctg accacaacgg                                                20
```

```
<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcgggtgga tgctgagaac a                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtcaatctc caccagtcgg g                                              21

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(1)
<223> OTHER INFORMATION: Fam-a
<220> FEATURE:
<221> NAME/KEY: modified_base
<222> LOCATION: (25)..(25)
<223> OTHER INFORMATION: a-BHQ1

<400> SEQUENCE: 15
atctacagtg aggagctgcg tgaga                                          25
```

PREPARATION AND AMPLIFICATION OF NUCLEIC ACIDS BY MEANS OF MAGNETIC PARTICLES

This application is a National Stage of PCT/EP2009/067882, filed Dec. 23, 2009 which claims priority to German Application No. 10 2008 055 120.1, filed Dec. 23, 2008, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 16, 2014, is named 0051-0044-US1_SL.txt and is 4,132 bytes in size.

RELATED APPLICATIONS

The invention relates to a preparation of a biological sample for performing detections and investigations.

For the preparation of a biological sample, it is known from the prior art to first make the contents of a biological sample accessible (known under the term "lysis" or "digestion"), to selectively bind constituents of the released contents of the biological sample on or to a solid support or carrier material (known under the term "binding"), to eliminate undesired constituents of the solid support or carrier material (known under the term "washing") and to dissolve the desired constituents, namely nucleic acids, subsequently from the solid support or carrier material (known under the term "elution"). At least one sought constituent, that is a defined part of a DNA or RNA strand, is finally duplicated, that is amplified, for example by means of a polymerase chain reaction (PCR).

The PCR process consists of a number of, for example, 25-50 cycles, which are performed in a thermocycler. The following details are guideline values. Usually, a PCR must be optimized for the specific reaction.

Each cycle consists of three steps:
1. Denaturation (melting): First the double-stranded DNA is heated to 94-96° C. to separate the strands. The hydrogen bonds, which hold together the two DNA strands, are broken. In the first cycle, the DNA is often heated for a relatively long time (initialization) to ensure that both the starting DNA and the primer have completely separated from one another and only single strands are present. Some (so-called hot start) polymerases must be activated by an even longer initial heating phase (up to 15 minutes).
2. Primer hybridization (primer annealing): The temperature is kept for about 30 seconds at a temperature that allows a specific addition of the primers to the DNA. The exact temperature is determined here by the length and the sequence of the primers (or the appropriate nucleotides in the primer if mutations are to be introduced by this=site-directed mutagenesis). If the temperature chosen is too low, the primers can under certain circumstances also add to non-100% complementary sequences and thus lead to non-specific products ("ghost bands"). If the temperature chosen is too high, the thermal motion of the primers under certain circumstances is so great that they cannot attach correctly so that no product formation at all or only inefficient product formation occurs. The temperature which largely excludes the two abovementioned effects is normally 2-3° C. below the melting point of the primer sequences; this usually corresponds to a temperature of 55-65° C.
3. Elongation (polymerization, extension, amplification): Finally, the DNA polymerase fills up the missing strands with free nucleotides. It begins at the 3'-end of the added primer and then follows the DNA strand. The primer is not detached again; it forms the start of the new single strand. The temperature depends on the working optimum of the DNA polymerase used (68-72° C.). This step lasts approximately 30 seconds per 500 base pairs, but varies as a function of the DNA polymerase used. Customary thermocyclers cool the reaction batches down to 4-8° C. after completion of all cycles, so that a PCR can be set up in the evening and the samples can be processed further on the morning after.

In the first cycle, initially DNA single strands result, which are longer in the 5'-direction than the target sequence. This can be explained by the fact that only a starting point (primer), but not an endpoint, is fixed exactly. The termination of the strand synthesis takes place here at the latest by the strand separation in the following denaturation step. The DNA employed and the DNA strands just formed are available in the second cycle. In the former, the same process takes place as in the first cycle. Primers now attach in the 5'-region to the newly formed DNA single strands, which 3' already end where they should. The strands now formed have no 5'-overlap, since the polymerase reads on the template in the direction of the 3'-end. At the end of the second cycle, there are thus products of the desired length for the first time. In the following cycles, the desired products replicate exponentially (as they themselves serve as a matrix for further strand syntheses), while the undesired long products (see products of the first cycle) only increase linearly (only DNA employed serves as a matrix). This is the theoretical ideal case; in practice, to a small extent, shorter fragments than the desired target DNA are also formed. These short fragments especially accumulate in the late cycles, whereby usually only approximately 30 cycles are run through to obtain all in all mainly DNA of the desired length and sequence.

A sample prepared in this way is identified subsequently to this, for example, by means of agarose gel electrophoresis. A gel is prepared, for example, by boiling agarose in a buffer, for example TBE buffer. Long threads of agarose polymers are in this way crosslinked to give a gel. In general, auxiliaries are added to the gels even during preparation for visualization of the separated molecules. In the case of DNA, these are usually ethidium bromide. By means of agarose gel electrophoresis, nucleic acid strands (RNA or DNA) are separated according to their size, and their sizes are determined by comparison with strands of known size. The more highly the agarose is concentrated, the smaller are the pores that are found in the gel. Gel electrophoresis functions like a sieve for molecules. An electrical field is used to pull the negatively charged nucleic acid molecules through the gel matrix, it being possible for the smaller molecules to move more rapidly through the gel and thus separation of the strands according to their size is made possible. On account of added auxiliaries, the nucleic acids separated in this way can generally be made visible with UV light. It can thus be determined whether a sought part of a DNA strand has been duplicated by the PCR and consequently whether the sample originally contained the sought DNA strands. Such detections are performed, inter alia, in paternity tests and in forensics.

For example, in the field of forensics generally only a restricted, small amount of sample material is available. In such cases it is important to obtain a high PCR sensitivity. The PCR sensitivity is a measure of the duplication of the sought part of a DNA strand. The more sensitive the PCR, the better and more rapidly the corresponding DNA strand is duplicated.

DETAILED DESCRIPTION OF THE INVENTION

Figure 1:
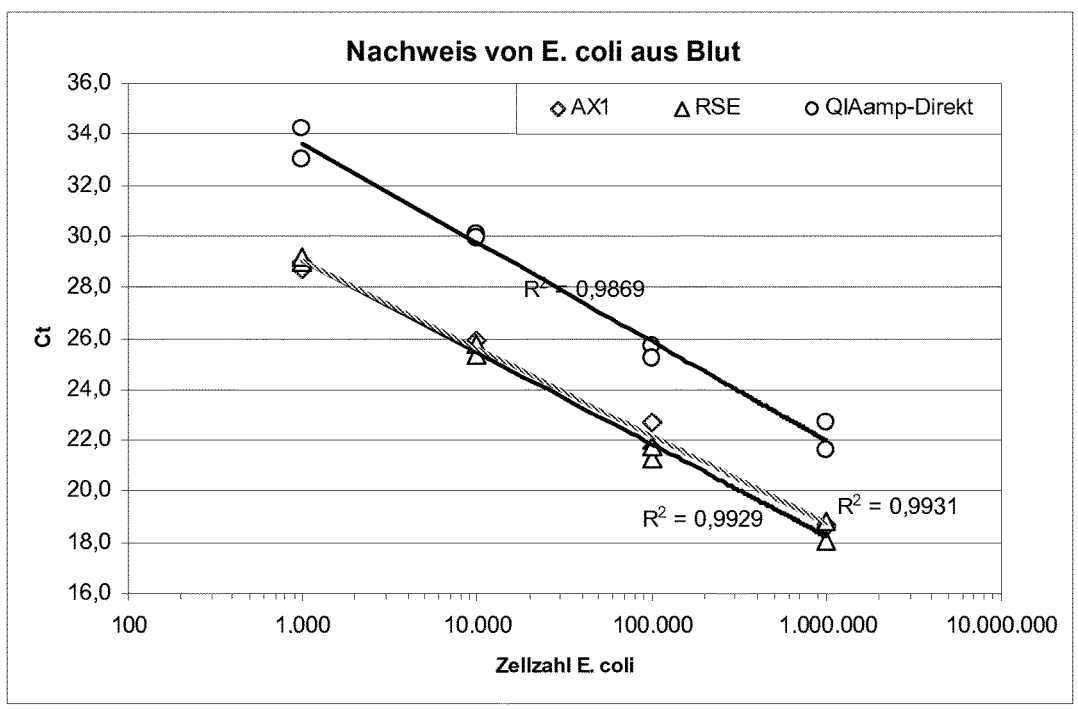
FIG. 1 provides the result of quantitative PCR for the detection of E. coli DNA from blood according to one aspect of the invention.

An automated process for the preparation of a biological sample, which comprises the steps lysis, binding, washing, elution and PCR, can be inferred from the European patent application having the official file reference EP08151152.9: A biological sample is transferred to a container that contains a filter consisting, for example, of a silica gel. Below the filter is provided an inlet or outlet for liquid. First, a biological sample is digested using a lysis buffer, in particular in this container. After the digestion of the sample, the lysis buffer is sucked off through the filter. It is simultaneously achieved thereby that the nucleic acid released by digestion binds to the filter. The binding of the nucleic acid to the filter is increased by a subsequent addition of ethanol to the vessel. With the aid of wash buffers, it is then washed to remove fats, lipids and proteins. After washing, the bound nucleic acid is dissolved from the filter with the aid of elution liquid. The elution liquid is supplied together with the nucleic acids now situated therein to a PCR chamber in order to carry out the desired polymerase chain reaction therein.

From the European patent application with the official file reference EP08151152.9, it furthermore emerges to separate the result of the PCR electrophoretically with the aid of an agarose gel and to stain the separated nucleic acid fragments in an ethidium bromide-containing water bath. By excitation with UV light, the stained nucleic acid fragments become visible and are thus detected. Binding takes place based on chaotropic chemistry. It is then bound under high salt (that is a solution having a high salt concentration). An ethanol elution takes place with low salt, that is a solution having a low salt concentration. If, on the other hand, an anion exchanger is employed, the binding takes place under low salt and elution under high salt.

The described preparation of a biological sample, which comprises said steps lysis, binding, washing, elution and PCR, is called a reference standard or else gold standard. A high PCR sensitivity can be achieved with the gold standard. A small amount of sample material then suffices to be able to adequately duplicate the DNA strand sought. In general, the reference standard comprises a standard nucleic acid preparation (with the steps lysis, binding, washing and elution) and subsequently a standard PCR and not the markedly more expensive, but also markedly more sensitive nested PCR, since the standard PCR for carrying out the desired detections generally suffices. PCRs are in principle susceptible to contamination by inhibitors, which can decrease the efficiency of the reaction. The advantage with a nested PCR is that even if the first PCR exhibits slight inhibition—a high sensitivity can be achieved by the second PCR which then generally proceeds without inhibition problems, despite primary inhibition in the first PCR. If, on the other hand, an "individual" PCR (reference standard), for example a qPCR, exhibits contamination by inhibitors, then the efficiency and thus also the sensitivity of the reaction is decreased. A problem, however, in the case of a nested PCR in comparison to the standard PCR, is the occurrence of cross-contamination. As a result of aerosols and other "accidents", the danger of false-positive results is very high in the case of the nested PCR.

A preparation of a biological sample according to the gold standard can further be inferred from the printed specification WO 93/11221. It is known from this to digest biological samples by use of enzymes, such as, for example, proteinase K, lysozyme and detergents such as SDS, Brij, Triton X-100, Tween 20, DOC and chemicals such as sodium hydroxide, guanidine hydrochloride and guanidine isothiocyanate. After the digestion and removal of undesired cell debris, the nucleic acid to be isolated is bound to an anion exchanger. It can further be inferred from the printed specification that after the binding, substances to be separated off are first removed by washing, in order then to detach again the bound nucleic acids with an elution buffer of high ionic strength. It can further be inferred from this prior art that the further process operations are only possible using buffer conditions which exhibit lower ionic strengths. In particular, before the performance of a PCR, the nucleic acid must first be desalted following the elution, which disadvantageously necessitates a correspondingly increased outlay. According to the printed specification WO 93/11221, a commercially available material can be selected as an anion exchanger, which allows binding of the nucleic acid to be isolated under the respective preparation conditions. The anion exchangers known from WO 93/11221 are preferably surface-modified carriers consisting of a matrix, preferably consisting of agarose, dextran, cellulose, acrylamide, polyvinyl alcohol, polystyrene, glass, alumina, titanium dioxide, zirconium dioxide or silica gel, such as, for example, DEAE-Q-Sepharose®, Q-Sepharose®, DEAE-Sephadex®, DEAE-Toyopearl®, Amberlite®, Nukleogen®. The anion exchangers can be porous carrier materials having an internal surface of high capacity suitable for interaction or non-porous carrier materials, which only enters into an interaction with the mixture to be separated on the external surface. Very particularly preferably, the anion exchanger is a material based on silica gel, which has a particle size of 1 to 250 μm, preferably 10 to 50 μm and very particularly preferably 15 to 25 μm and a pore diameter of 1 to 2500 nm, preferably 10 to 500 nm, particularly preferably 100 to 400 nm. A material having high surface charge and high binding capacity for nucleic acids has in particular proven to be an anion exchange material.

The modification of the silica gel is performed according to WO 93/11221, preferably by silanization of the carrier material, such as disclosed, for example, in EPA 83 901 065, DE-A-39 35 098 and U.S. Pat. No. 5,057,426, In EP-A 83 901 065, for example, gamma-glycidyloxypropyltrimethoxysilane and N,N-dimethylaminoethanol are used for the modification of the carrier material.

If the PCR sensitivity obtained according to the gold standard comprising the standard PCR does not suffice, the markedly more sensitive nested PCR is performed, in which two PCR reactions are connected one after the other. An aliquot of the PCR product from the first amplification serves as a matrix for the second PCR. In this, a shorter DNA fragment is amplified by a second primer pair, which binds to sequence regions within this matrix (nested primer). The advantage of the nested PCR compared to the standard PCR is a sensitivity increased by 2-3 powers of ten paired with increased specificity, as for the nested PCR product only the product of the first amplification can serve as a matrix. The smallest traces of DNA can also be detected using this method and diagnostic aims can be made accessible. With optimal adjustment of a nested PCR, even 1 to a few matrixes suffice for amplification depending on the target sequence and object. In comparison to the standard PCR, however, additional process steps must disadvantageously be performed. If the PCR sensitivity of a sample preparation according to the gold standard does not suffice with the standard PCR, a process would then be desirable which makes possible an improved PCR sensitivity, without having to increase the necessary outlay.

Indeed, there are alternative processes which lead to good PCR sensitivities without an outlay having to be made for this, which corresponds to the gold standard with a nested PCR. Thus, for example, the printed specification WO 92/17609 A1 discloses a process for the determination of target cells, in which the cells are first bound intact to magnetic grains—known under the term "magnetic beads"—with the aid of antibodies and thus enriched. Such processes, however, are very specific and can therefore only be employed to a relatively restricted extent.

The object of the invention is the creation of a simple process for the preparation of a biological sample having high PCR sensitivity.

The object is achieved by a process having the features of claim 1. Advantageous embodiments result from the subclaims.

To achieve the object, a process for the preparation of a biological sample comprises the steps lysis, binding, optional washing and a two-stage amplification. During the first amplification, the sought DNA strands are amplified relatively unspecifically. The relatively unspecifically amplified DNA strands thus obtained are subsequently amplified specifically. The two-stage amplification is in particular a nested PCR. Differing from the gold standard, the elution and the in many cases subsequent desalting of the solution resulting from the elution are unnecessary. Indeed, a two-stage amplification such as the nested PCR in comparison to the standard PCR necessitates an additional technical and temporal outlay. This is compensated, however, in the process according to the invention by the elution in addition to desalting being unnecessary. Altogether, the necessary outlay according to the invention corresponds to the outlay that is necessary in the maintenance of the gold standard using standard PCR. However, in comparison to the gold standard comprising a standard PCR, the PCR sensitivity can be markedly increased. Altogether, the ratio of outlay to benefit can therefore be increased using the process according to the invention. The process according to the invention can comprise the steps and devices known from the prior art provided these do not counteract the performance of the process according to the invention. Thus, for example, the lysis buffer or anion exchanger mentioned at the outset can be used. Thus the lysis in addition to binding can take place on preferably magnetic silica particles in a known manner by means of chaotropic salts and by means of ethanol. The lysis can be assisted mechanically, in fact preferably by ultrasound, or by stirring with the aid of a magnetically driven stirring rod, in order to mechanically assist a digestion rapidly and simply.

Instead of a PCR, other amplification processes can also be performed, thus, for example, WGA (whole genome amplification) or reverse transcription. However, a nested PCR is preferably performed, or a nested PCR in which the first PCR comprises a one-step RT PCR.

PCR, however, is the most robust process for the two-stage amplification process. For the person skilled in the art, it is possible in principle to carry out the first and the second nucleic acid amplification also using processes that are not based on the use of a heat-stable polymerase and multistage temperature steps (that is on PCR). Such processes for the amplification of DNA area "Helix-dependent Amplification" (HDA); "Recombinase Polymerase Amplification" (RPA); "Sequence-Specific Rolling Circle Amplification" (RCA); "Loop-mediated Isothermal Amplification" (LAMP). For the amplification of RNA, methods such as "Signal Mediated Amplification of RNA Technology" (SMART) or "Nucleic acid sequence-based amplification" (NASBA) can also be used alternatively to simple reverse transcription. Of course, it is also possible for the person skilled in the art to combine these and other known processes for amplification according to need. The first and the second amplification can also be designed as multiplex amplifications.

Specific amplifying means that in the ideal case only one amplicon is duplicated. "Unspecific amplifying" means a simultaneous and unspecified amplification of a number of gene sequences by an incomplete hybridization of the primers, i.e. the primers also bind incompletely with "mismatch" in the first, cycles of the PCR to the starting nucleic acid and are lengthened by the polymerase. These "wrong" amplificates can function again as templates in the course of the PCR (the primers then bind perfectly) and are then amplified—this then manifests itself in the form of byproducts in the PCR.

Preferably, the binding takes place by means of anion exchange, since even during the lysis binding can take place. This embodiment of the invention contributes to the fact that the process can be performed easily in a closed, very small microfluidic system. According to the prior art, the binding by means of anion exchange is indeed linked to the disadvantage that the elution necessitates the use of salts of high concentration, which makes desalting necessary following the elution. Since elution is unnecessary according to the invention, a subsequent desalting is also unnecessary.

In order to be able to supply the bound nucleic acid suitably to a nested PCR, the bound nucleic acid is separated after the binding in one embodiment of the invention, by, for example, centrifuging particles to which the nucleic acid is bound. The supernatant, that is the buffer last used or the solution last used, is discarded. If, for example, it was previously washed, the wash buffers are thus removed by final discarding of the supernatant. The PCR sensitivity is increased by the separation. For example, a sample contains $10^3$ bacteria or viruses. According to the prior art, a lysate of typically 1.5 ml total amount is obtained from this. Of this, however, a PCR can be performed only with 1 to 3 microliters. The consequence of this is that only 0 to 1 copy(ies) can get to a PCR 1. This small amount can lead to sensitivity problems. By means of the concentration according to the invention, it is achieved that approximately quantitatively $10^3$ copies of the PCR 1 are supplied and thus contribute to achieving the surprisingly high sensitivity.

In one embodiment of the invention, the aforementioned bodies are magnetic particles ("magnetic beads"). The desired separation or concentration can thereby be performed particularly rapidly, namely, for example, with devices known from the prior art provided for this. To this end, for example, a tube used for carrying out the preceding steps is inserted in a commercially obtainable device. The permanent magnets positioned thereon attract the magnetic particles to the wall of the tube. The supernatant can thus be safely removed after such a magnetic separation. The supernatant is in turn discarded. Using the separated constituents, which comprise the magnetic particles in addition to the nucleic acids bound thereto, a PCR 1, for example, that is the first stage of a nested PCR, is performed. This embodiment of the invention further contributes to the fact that the process can be performed in a simple manner in a closed, microfluidic system. A magnet is then located in a first PCR chamber, subsequently also called a central magnet. This central magnet is larger than the diameter of exit channels or else the exit channels are separated from the first PCR chamber by a sieve or a frit. If the magnetic particles with the nucleic acids bound thereto are now transported into the first PCR chamber with the aid of a liquid, the magnetic particles, that is the magnetic beads, stick to the magnet. If the liquid is aspirated from the first PCR chamber, the desired separation thus takes place. The channel diameters of the channels leading off or the pore width of the frit or of the sieve are chosen such that the central magnet located in the chamber, to which no nucleic acids are bound, is restrained. Since only a relatively large magnet with magnetic grains or beads adhering thereto must be restrained, the danger also does not exist that exit channels or sieves can be added disadvantageously. In principle, the process can also be performed, however, using non-magnetic grains or beads, which are then separated by a sieve in the PCR chamber from the solution or liquid with which the beads or grains were previously transported into the first PCR chamber.

Following a performed PCR 1 of a nested PCR, separation again takes place, which in the case of magnetic particles employed takes place particularly simply with the aid of a magnet. The supernatant contains amplicons, that is DNA strands, which have been duplicated by the PCR 1. An aliquot of the supernatant, that is a part of the supernatant, is added to the PCR 2. The nested PCR is continued here in a manner known from the prior art.

In one embodiment of the invention, the process is performed completely or at least mainly in a closed system, which already comprises the PCR reagents needed, namely in particular in dried form. It is then essential that the nested PCR or an equivalent two-stage amplification process is especially performed in a closed system, which can in particular then be realized technically without difficulty in a disturbance-free manner if the nucleic acids are bound to magnetic particles. Indeed, a nested PCR is very sensitive, but the nested PCR, however, has a disadvantage, especially because of its high sensitivity—it is very susceptible to contamination. As a result of unwanted spread of amplicons and their de novo amplification, false-positive results can easily occur. In order to guard against these difficulties, it is advantageous to carry out the PCR reaction in a closed system with PCR reagents contained therein. False-positive results can thus be minimized.

The process can even be performed in a microfluidic system, which then minimizes even the space requirement.

In one embodiment of the invention, the lysis buffer employed has a salt content of in total less than 50 millimolar, that is 50 millimoles/liter. It has turned out that by observing this limit the PCR sensitivity can be markedly increased.

The pH of the lysis buffer used is preferably adjusted to values between pH 7.5 to 9.5. This also increases the PCR sensitivity. In order to stabilize the pH in the manner mentioned, commercially obtainable buffers tris, hepes and/or mops are preferably employed, in particular with a concentration of 10 to 20 millimolar, in order to achieve good PCR sensitivities. The aforementioned designations are abbreviations which are familiar to the person skilled in the art.

As detergents, in one embodiment of the invention nonionic detergents are employed for performing the lysis. Suitable nonionic detergents are marketed commercially under the trade names Tween®, Nonidet P-40 or Brij®. This selection also makes it possible to achieve good PCR sensitivities.

The concentration of nonionic detergents is preferably 0.1 to 0.4% by volume.

Optionally, polyvinylpyrrolidone (abbreviated as PVP) and namely in particular from 0.05 up to 0.1% by volume is added to the lysis buffer. Inhibitors are bound by PVP and good PCR sensitivity is obtained in a further improved manner.

A simple process for the preparation of a biological sample having an always still relatively high PCR sensitivity can also be achieved by binding the nucleic acid obtained by digestion to particles, separating the particles with the nucleic acids bound thereto and amplifying the bound nucleic acids. The amplification can then also take place by means of a conventional process such as, for example, a qPCR, that is a process in which a quantitative evaluation takes place only after completion of the PCR. A relatively high sensitivity is especially achieved if the lysis buffer is suitably chosen. A suitably chosen lysis buffer in particular comprises the features of a lysis buffer indicated in subclaims. However, other isothermal amplifications can also be performed.

The invention is illustrated in more detail below with the aid of examples.

Anion exchange particles (namely RSE anion exchange beads or grains) for the binding of nucleic acid were prepared as follows, the preparation basis of these particles being described in the patent application: WO 2007/065933 A1:

As a preparation, 302 ml each of SPAN 85 are dissolved in 13 l of Norpar 12 and 1.9 l of viscous paraffin. Subsequently, 112.5 ml of EGDMA and 261 ml of GMA, which have been freed from inhibitors beforehand, are added to a 2000 ml Nalgene bottle or a 2000 ml beaker, 370 ml of ethylene glycol, 11.25 g of AIBN and 279 g of Bayoxide E 5706 are added and the mixture is homogenized for 2 minutes at the highest setting in an IKA Ultra Turrax. A quarter of the Norpar solution is added to a 5000 ml plastic vessel in four portions and the vessel is connected to a homogenizer. One quarter each of an iron oxide suspension is added at the lowest setting and the mixture is homogenized for 60 seconds under full power. The emulsion is then in each case transferred to a 20 l reactor with a reflux condenser, KPG stirrer and a line for passing gas through at 250 rpm and the speed of rotation of the stirrer is increased to 300 rpm. The iron oxide emulsion in organic solvent is then subsequently added slowly, the mixture is degassed for 5 minutes by passing through nitrogen, the stirrer is speeded up to 350 rpm, and the mixture is then stirred overnight at 350 rpm. Heating is already begun while passing through gas, then the mixture is kept at 70° C. for one hour, then overnight at 80° C.

The next morning, the quantities of organic solvent are filtered off through a suction filter with a polyethylene frit and the oil residues are stored. The magnetic residue is then washed three times with acetone, additionally waiting about 10 minutes after acetone addition here before filtering off with suction. The residue is then taken up in completely demineralized water, washed three times with water, and washed once again with acetone and twice with abs. ethanol, and the solvents are separated off here using magnetic separation, stirring up here and allowing the solvent to act for 5 minutes. In the first water washing step, ultrasound is allowed to act on the vessels for 10 minutes in an ultrasonic bath and the separation is then continued. After the last water step and the last three acetone and ethanol steps, the liquid is basically separated off, or the particles are allowed to stand in the last ethanol solution. In order to determine the yield, a portion is removed from the last suspension and dried for determination of the solids content. The finished product has an average particle size distribution of 10 µm.

First, a polymer suspension containing 2.5 g in ethanol is added to a glass filter funnel, porosity 4 and washed four times with anhydrous diglyme or toluene. The residue is taken up in 50 ml of an almost 10% strength solution of bis-tris or diisopropylaminoethylamine in anhydrous diglyme or toluene and transferred to a 100 ml three-necked flask. A reflux condenser is then attached to the flask, the latter is briefly degassed twice and the mixture is then allowed to react overnight (16 h) at 100 rpm and 120° C. The next morning, the polymers are washed four times with completely demineralized water, three times with ethanol and the polymers are then stored under ethanol.

A further type of functionalized anion exchanger magnetic particle (AX1) is synthesized as follows.

A suspension of MagAttract "G" (from BioSprint DNA blood kit 96, QIAGEN, item #940057) is employed and washed four times with Millipore water. The supernatants are separated off here by means of magnetic separation and discarded. Subsequently, 2.5 g of the dried magnetic particles are resuspended in 25 ml of dry γ-glycidoxypropyltriethoxysilane (Aldrich, item #4401.67). The mixture is then briefly degassed on a rotary evaporator and aerated with nitrogen. Subsequently, the bath is heated to 140° C. and the sample is allowed to react on the rotary evaporator for eight hours. The product is then separated magnetically and the supernatants are washed four times with dry dioxane. The magnetic silica gel is then suspended in 25 ml of dry dimethylaminoethanol and treated with 250 µl of boron trifluoride etherate. Subsequently, the product mixture is heated under reflux for 24 hours on the rotary evaporator and magnetically separated after cooling, the supernatants being discarded. It is then washed repeatedly with dioxane, methanol and diethyl ether and dried at 50° C. in a vacuum drying oven.

In order to determine the sensitivity of the process according to the invention, a real-time PCR is performed as PCR 2 in the following examples, with which the DNA obtained is quantified.

The real-time PCR is a duplication method for nucleic acids, which is based on the principle of the conventional polymerase chain reaction (PCR), and additionally makes possible the quantification of the DNA obtained. The quantification is performed with the aid of fluorescence measurements, which are determined during a PCR cycle. The fluorescence increases proportionally with the amount of the PCR products. At the end of a run (which consists of several cycles) the quantification in the exponential phase of the PCR is performed by means of fluorescence signals obtained. Only in the exponential phase of the PCR (which lasts for only a few cycles in a run) is the correct quantification possible, since during this phase the optimal reaction conditions prevail. This method thus differs from other quantitative PCR methods (qPCR), which perform a quantitative evaluation (e.g. competitive PCR), usually involving a gel-electrophoretic separation of the PCR fragments, only after completion of the PCR.

In the first phase of the amplification of a PCR, the template amount is restricted and the probability that template, primer and polymerase meet is suboptimal, while in the third phase of the amplification the amount of the products (DNA, pyrophosphate, monophosphate nucleotides) increases such that inhibition by this occurs, product fragments hybridize with one another more frequently, the substrates are slowly consumed and finally the polymerases and nucleotides are slowly destroyed by the heat. An exponential and therefore quantifiable increase is found only in the phase in between. Exponentially, a PCR remains at 12 to 400 starting copies for about 30 cycles, at 200 to 3200 for 25 cycles and at initially 3200 to 51,200 for at most 20 cycles. In order always to be able to measure at the start of the exponential phase, frequently the CT value (threshold cycle) or the Cp value (crossing point) is used, which describes the cycle in which the fluorescence for the first time increases significantly above the background fluorescence.

In the course of a first exemplary embodiment, the bacterium *Escherichia coli* was diluted in blood and investigated. Experiments were performed using the different anion exchange speeds mentioned in order to investigate whether the choice of the anion exchange beads influences the result with differing surface modification.

The following materials were employed:
AX1 anion exchange beads
RSE anion exchange beads
blood from blood bag
lysis buffer GE (01% PVP MW 10,000; 0.45% Tween-20; 0.45% NP-40; 10 mM tris/Cl pH 7.5; 1 mM EDTA)
*Escherichia coli* O157:H7 (ATTC 700728; apathogenic strain)
dilutions: $10^8$/ml; $10^7$/ml; $10^6$/ml; $10^5$/ml;

```
PCR primers
EOF: ATGCTACCCCTGAAAAACTC

EOR: CGCTTGAACTGATTTCCTC

EFwd: CGATGATGCTACCCCTGAAAAACT

ERev: TATTGTCGCTTGAACTGATTTCCTC

EPro: "6-Fam"-CGTTGTTAAGTCAATGGAAAACCTG-BHQ1
```

The experiment was performed according to the following protocol:

In each case 100 µl of blood and 10 µl of a dilute *E. coli* overnight culture are filled into various 1.5 ml microtubes, that is into small, tubular vessels. The dilutions were $10^8$/ml;

$10^7$/ml; $10^6$/ml; $10^5$/ml. 1 ml of buffer GE and 20 µl of proteinase K and 10 µl of lysozyme (10 mg/ml) were filled into the microtubes.

20 µl of anion exchange magnetic particles (50 mg/ml) were added to the microtubes, namely, depending on batch, either AX1 or RSE magnetic particles. An incubation was subsequently performed by treating the microtubes for 30 min on an Eppendorf thermomixer at 56° C. and 1400 revolutions per minute. The incubation was then continued, namely for 10 min on the Eppendorf thermomixer at 80° C. and 1400 revolutions per minute. The sample is digested and bound by this treatment.

The tubes are then inserted into a magnetic separation device. For 20 sec, the magnetic particles are allowed to deposit on the wall of the tube by the action of the magnetic field of the permanent magnets of the device. The supernatant is now pipetted off and discarded. Subsequently, the magnetic particles are washed twice with buffer GE. For this, 800 µl each of buffer GE are pipetted into the tube and the magnetic particle sediment is resuspended by brief vortexing. Next, a magnetic separation is performed and the supernatant is again discarded.

The magnetic particle sediment is now resuspended by brief vortexing in 100 µl of double-distilled, that is twice-distilled, water and transferred to a PCR tube. The supernatant is removed carefully and quantitatively. The magnetic beads are resuspended with 50 µl of PCR solution and the first PCR is started and performed as follows:

25 µl of Hot Star Tag Master Mix (QIAGEN), 1 µl of EOF (100 µM), 1 µl of EOR (100 µM) and 23 µl of water are added. After activation of the Tag polymerase for the first time by incubation at 95° C. for 15 min, a total of 20 temperature cycles are performed. A cycle comprises the following steps:

Denaturation 15 s; 95° C.
Annealing 30 s; 52° C.
Extension 15 s; 72° C.

After PCR1, the PCR tube is inserted onto a magnetic separation rack and 5 µl of supernatant are transferred to a fresh PCR tube.

The second PCR, namely a quantitative real-time PCR, is begun with an addition of 20 µl of PCR 2 reagents. The following reagents are employed:

12.5 µl of QIAGEN QuantiTect sample PCR Mastermix, 0.1 µl of EFwd; 0.10 µl of ERev; 0.05 µl of EPro and 7.25 µl of double-distilled water. After the Tag polymerase activation for 5 min at 95° C., a total of 40 cycles are performed. A cycle comprises the following steps: (denaturation 15 s; 95° C.; extension 60 s; 60° C.).

As a comparison experiment, a preparation according to the gold standard was performed with a standard PCR with according to the commercially obtainable "QIAamp DNA Blood Mini Kit", 10 µl of *E. coli* dilution were prepared together with 100 µl of blood according to the standard protocol and eluted with 100 µl of elution buffer.

The result of the quantitative PCR for the detection of *E. coli* DNA according to example 1 using different numbers of bacteria in the preparation is shown in FIG. 1 and compared with the result that was obtained by the standard preparation using elution and standard PPCR. The ct values obtained according to the invention were around about two units below the ct values that were obtained on account of the standard process. Since the sensitivity is all the better, the lower the ct value, despite comparable outlay the sensitivity was thus improved by the process according to the invention. The test series further illustrate that using the process according to the invention, a good linearity can be achieved that reflects the dynamic range of the PCR detection system. In this respect too, a very good result was thus achieved. Finally, the result illustrates that the result does not depend substantially on the choice of the anion exchange beads.

In the course of a second exemplary embodiment, the bacterium *Escherichia coli* was diluted in SurePath medium and prepared and investigated as follows according to the invention and—for the purpose of comparison—according to the prior art.

Material Used:
AX1 anion exchange beads
RSE anion exchange beads
blood from blood bag
lysis buffer GE (01% PVP MW 10,000; 0.45% Tween-20; 0.45% NP-40; 10 mM tris/Cl pH 7.5; 1 mM EDTA)
*Escherichia coli* O157:H7 (ATTC 700728; apathogenic strain)
dilutions: $10^8$/ml; $10^7$/ml; $10^8$/ml; $10^5$/ml;

```
PCR primers
EOF: ATGCTACCCCTGAAAAACTC

EOR: CGCTTGAACTGATTTCCTC

EFwd: CGATGATGCTACCCCTGAAAAACT

ERev: TATTGTCGCTTGAACTGATTTCCTC

EPro: "6-Fam"-CGTTGTTAAGTCAATGGAAAACCTG-EHQ1
```

The following were prepared according to the following protocol

100 µl of blood and 10 µl of *E. coli* overnight culture are added in various dilutions to a 1.5 ml microtube
addition of 1 ml of buffer GE and 20 µl of proteinase K and 10 µl of lysozyme (10 mg/ml)
addition of 20 µl of MagBeads
incubation: 30 min on Eppendorf thermomixer at 56° C. and 1400 rpm
incubation: 10 min on Eppendorf thermomixer at 80° C. and 1400 rpm
magnetic separation and discarding of the supernatant
wash Mag Beads 2× with buffer GE (800 µl each; briefly vortex; magnetic separation and discarding of the supernatant)
resuspend MagBead sediment in 100 µl of double-distilled water and transfer to a PCR tube
remove supernatant carefully and quantitatively
resuspend beads with 50 µl of PCR solution and start PCR1
Nested PCR1
25 µl of Hot Star Tag Master Mix (QIAGEN)
1 µl of EOF (100 µM)
1 µl of EOR (100 µM)
23 µl of water
Tag activation 15 min; 95° C.
Cycle:
denaturation 15 s; 95° C.
annealing 30 s; 52° C.
extension 15 s; 72° C.
number of cycles 20
After PCR1: place PCR tube on magnetic separation rack and transfer 5 µl to a fresh PCR tube
carrying out PCR2 (quantitative real-time PCR) by addition of 20 µl of PCR 2 reagents:
12.5 µl of QIAGEN QuantiTect sample PCR Mastermix, 001 µl of EFwd; 0.10 µl of ERev; 0.05 µl of EPro, 7.25 µl of double-distilled water; cycling: Taq activation 5 min; 95° C.; 40 cycles [denaturation 15 s; 95° C.; extension 60 s; 60° C.]

Control experiment according to the prior art: QIAamp [10 µl of *E. coli* dilution in 100 µl of blood were prepared according to standard protocol and eluted with 100 µl]. "QIAamp nested:" 5 µl of the eluate were employed in PCR1 and of this 5 µl were again employed in PCR2: "QIAamp direct 5 µl of the eluate were employed in PCR 2".

Figure 2:
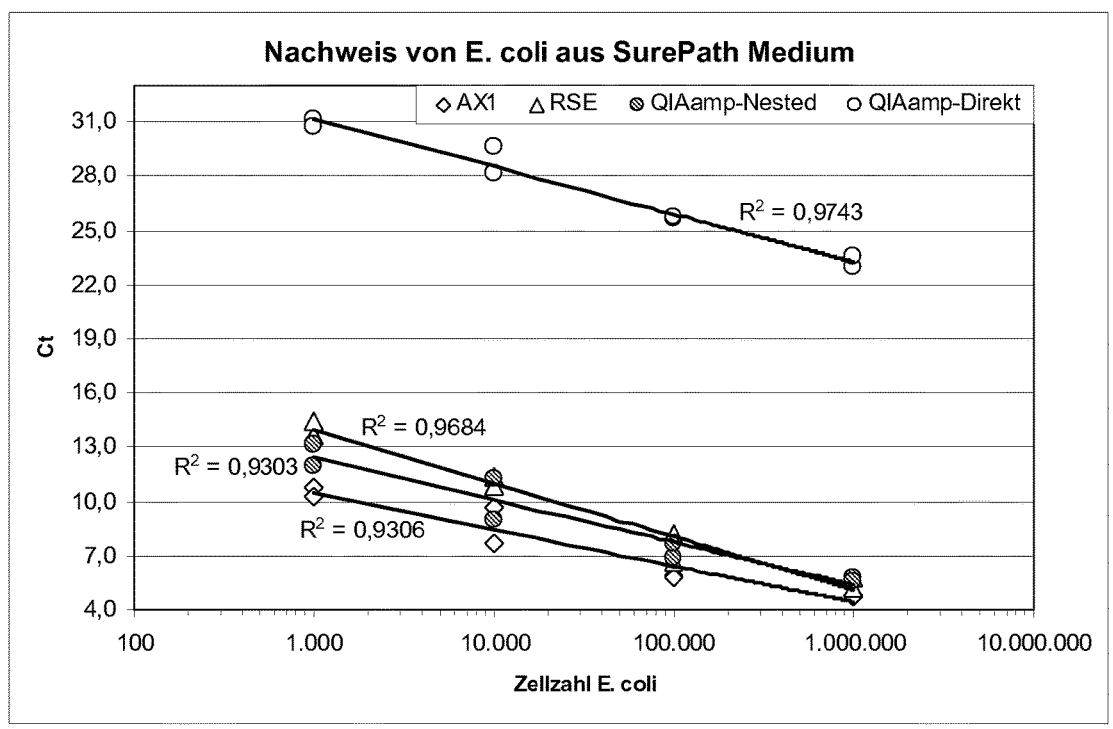
FIG. 2 shows the result of the quantitative PCR for the detection of E. coli DNA from SurePath medium.

FIG. 2 shows the result of the quantitative PCR for the detection of *E. coli* DNA from example 2 with different numbers of bacteria in the preparation. From the result thus achieved, it is surprising that even the sensitivity was achieved that was achieved by a sample preparation according to the gold standard using a nested PCR (QIAamp nested). In turn, a great linearity was also obtained. The result from example 1 was further confirmed that it was possible to markedly increase the sensitivity compared to the standard process using the standard PCR (QIAamp direct) without having to increase the outlay for this.

In the course of a third exemplary embodiment, SIHA cells were prepared and investigated in SurePath medium.

The materials employed were
  Cultured SIHA cells (human cervical carcinoma cell line; 2-3 copies of HPV16/cell; ATCC: HTB 35).

The cells were cultured in cell culture flasks by means of standard cell culture protocols. After washing with PSB, the cells were trypsinized and the cell count was determined under the microscope. $10^6$ cells in each case were aliquotted and sedimented by centrifugation. After the removal of the supernatant, the cells were frozen as a sediment. For preparation, the cells sediments were resuspended by addition of SurePath medium. Further dilutions were in each case prepared using SurePath medium.
  AX1 anion exchange beads
  RSE anion exchange beads
  Lysis buffer GE (01% PVP MW 10,000; 0.45% Tween-20; 0.45% NP-40; 10 mM tris/Cl pH 7.5; 1 mM EDTA)

```
PCR primers
16oFWD       CACCAAAAGAGAACTGCAATG

16iFWD       GGAGCGACCCAGAAAGTTACCAC

16oREV       GGATTCCCATCTCTATATACTA

16iREV       GCATAAATCCCGAAAAGCAAAGTCA

16PRO        AGAATGTGTGTACTGCAAGCAACAG[BHQ-FAM]
```

The procedure was as follows according to the following protocol:
  500 µl of SurePath medium containing SIHAs cells in various dilutions are added to a 2.2 ml microtube
  addition of 1 ml of buffer GE and 20 µl of proteinase K
  addition of 20 µl of MagBeads
  incubation: 30 min on an Eppendorf thermomixer at 56° C. and 1400 rpm
  incubation: 10 min on an Eppendorf thermomixer at BOC and 1400 rpm
  magnetic separation and discarding of the supernatant
  wash Mag Beads 2× with buffer GE (800 µl each; briefly vortex; magnetic separation and discarding of the supernatant)
  resuspend MagBead sediment in 100 µl of double-distilled water and transfer to a PCR tube
  carefully and quantitatively remove supernatant
  resuspend beads using 50 µl of PCR solution and start PCR1

Nested PCR1:
  25 µl of Hot Star Taq Master Mix (QIAGEN)
  1 µl of 16oFWD (100 µM)
  1 µl of 16oREV (100 µM)
  23 µl of water
  Cycling
  Taq activation 15 min; 95° C.
  denaturation 15 s; 95° C.
  annealing 30 s; 52° C.
  extension 15 s; 72° C.
  number of cycles 20
  After PCR1; place the PCR tube on the magnetic separation rack and transfer 5 µl to a fresh PCR tube
  performing PCR2 (quantitative real-time PCR) by addition of 20 µl of PCR 2 reagents:
  12.5 µl of QIAGEN QuantiTect sample PCR Mastermix, 0.1 µl of 16iFWD; 0.10 µl of 16iRev; 0.05 µl of 16iPro, 7.25 µl of double-distilled water; cycling: Taq activation 5 min; 95° C.: 40 cycles [denaturation 15 s; 95° C.; extension 60 s; 60° C.]

Comparison experiments: QIAamp [500 µl of SurePath medium with SIHAs cells prepared, according to standard QIAamp protocol and eluted with 100 µl). "QIAamp nested" 5 µl of the eluate were employed in PCR1 and of this again 5 µl in PCR2.

Figure 3:
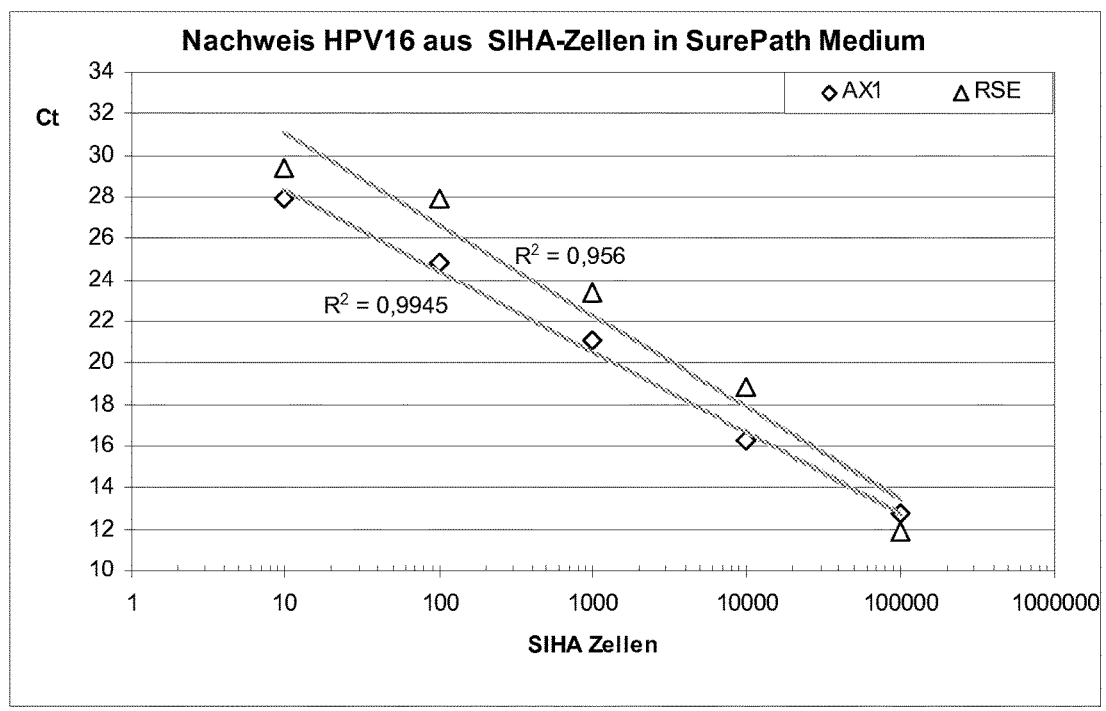
FIG. 3 shows the result of the quantitative PCR for the detection of HPV16 from SIHA cells.

FIG. 3 shows the result of the quantitative PCR for the detection of HPV16 from SIHA cells from exemplary embodiment 3 using different SIHA cell counts in the preparation.

Conclusion: The strategy of "nested PCR bead cycling" for the preparation of HPV16 from SurePath medium shows a high linearity of detection of cells employed. Up to 100 cells can be safely detected. The process according to the invention is thus also suitable for HPV diagnosis.

In the course of a fourth exemplary embodiment, the binding and amplification were performed by means of silica MagBeads.

The following were employed as materials:
  MasG MagAttract suspension G; QIAGEN
  MasB: MagAttract suspension B; QIAGEN
  SurePath medium (BD)
  lysis buffer G (3 M GITC; 20% NP-40)
  *Escherichia coli* O157:H7 (ATTC 700728; apathogenic strain)
    dilutions: $10^8$/ml; $10^7$/ml; $10^6$/ml; $10^5$/ml

```
PCR primers
EOF:  ATGCTACCCCTGAAAAACTC

EOR:  CGCTTGAACTGATTTCCTC

EFwd: CGATGATGCTACCCCTGAAAAACT

ERev: TATTGTCGCTTGAACTGATTTCCTC

EPro: "6-Fam"-CGTTGTTAAGTCAATGGAAAACCTG-BHQ1
```

The procedure was according to the following protocol:
  500 µl of SurePath medium and 10 µl of *E. coli* overnight culture are added in various dilutions to a 1.5 ml microtube
  addition of 500 µl of buffer G and 20 µl of proteinase K (QIAGEN)
  incubation: 20 min 56° C.
  addition of 500 µl of isopropanol and 20 µl of silica magnetic particles (MasG or MasB)

shaking at 1400 rpm on an Eppendorf thermomixer for 10 min magnetic separation and discarding of the supernatant resuspend MagBead sediment in 100 µl of buffer AW2 (QIAGEN) and transfer to a PCR tube magnetic separation and discarding of the supernatant rinsing of the bead under separated state with 3×150 µl of double-distilled water carefully and quantitatively remove supernatant resuspend beads with 50 µl of PCR solution and start PCR1

Nested PCR1:

25 µl of Hot Star Tag Master Mix (QIAGEN)

1 µl of EOF (100 µM)

1 µl of EOR (100 µM)

23 µl of water

Tag activation 15 min; 95° C.

Cycle:

denaturation 15 s;

annealing 30 s; 52° C.

extension 15 s; 72° C.

number of cycles 20

After PCR1: place PCR tube on the magnetic separations rack and transfer 5 µl to a fresh PCR tube performing PCR2 (quantitative real-time PCR) by addition of 20 µl of PCR 2 reagents 12.5 µl of QIAGEN QuantiTect sample PCR Malta mix, 0.1 µl of EFwd; 0.10 µl of ERev; 0.05 µl of EPro, 7.25 µl of double-distilled water; cycling: Tag activation 5 min; 95° C.; 40 cycles [denaturation 15 s; 95° C.; extension 60 s; 60° C.]

Figure 4:
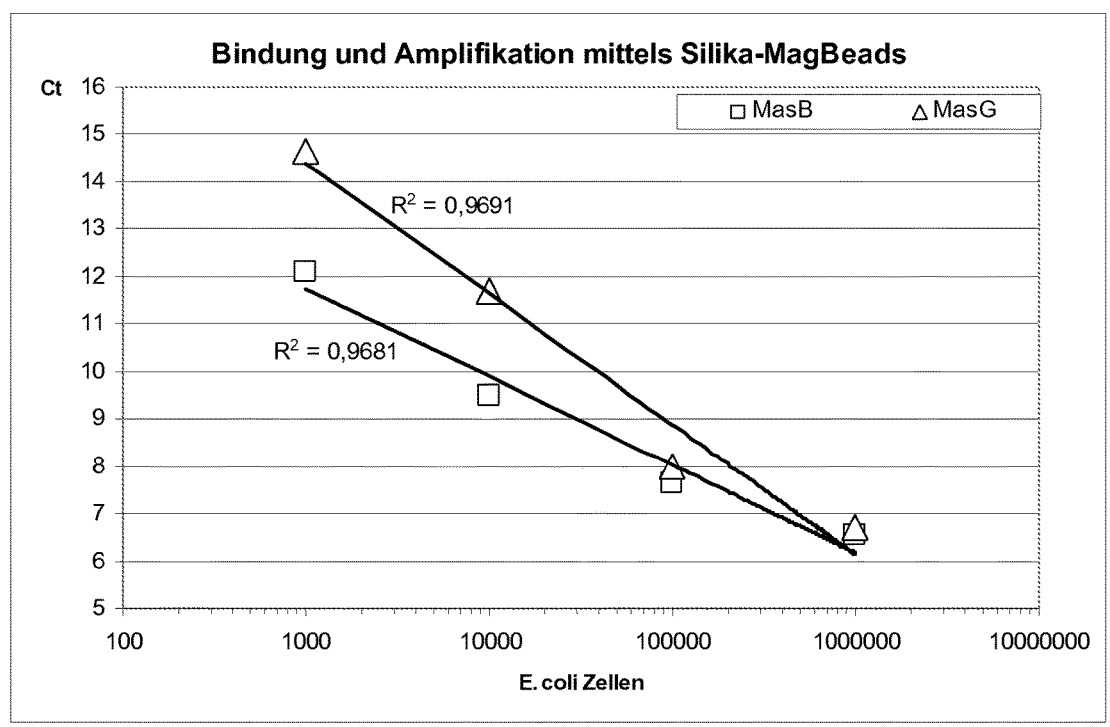
FIG. 4 depicts the results of the quantitative PCR for the detection of E. coli DNA in which the binding and amplification of the DNA is by means of silica MagBeads.

FIG. 4 clarifies the result of the quantitative PCR for the detection of *E. coli* DNA from exemplary embodiment 4 with a different number of bacteria in the preparation. In addition to the use of anion exchange magnetic particles, it was also shown that the inventive process can in principle also be performed using silica magnetic particles and chaotropic nucleic acid binding.

In the course of a fifth exemplary embodiment, the RNA isolation and its detection are to be determined by means of the RNA bacteriophages "fr".

For this, 500 µl of phage fr suspension [$5 \times 10^6$ PFU (plaque forming units)] and 1 ml of lysis buffer GE (01% PVP MW 10,000; 0.45% Tween-20; 0.45% NP-40; 10 mM tris/Cl pH 7.5; 1 mM EDTA), 20 µl of proteinase K and 20 µl of AX01 beads were mixed in a 1.5 ml microtube.

First, the reagent vessel is incubated on an Eppendorf thermomixer at 56° C. and 1400 rpm for 15 min. After a magnetic separation, the supernatant is discarded and the magnetic particles are washed twice with buffer GE (800 µl each; briefly vortex; magnetic separation and discarding of the supernatant). The magnetic particle sediment is now resuspended in 1× QuantiTect sample RT-PCR Master Mix (QIAGEN GmbH) and transferred to a PCR tube. After a further magnetic separation, the supernatant is again quantitatively removed and the reaction is started by addition and resuspension of the sediment in 50 µl of RT-PCR solution.

The RT-PCR mix is composed as follows:

25 µl of 2× Quantitect sample RT-PCR Master Mix 0.5 µl of FOF (CTCGAAGTTTACCAATCAAT (SEQ ID NO: 11); 10 µM)

0.5 µl of FOR (TATTTATCTGACCACAACGG (SEQ ID NO: 12); 10 µM)

0.5 µl of RT mix 23.5 µl of water

For the RT-PCR the following temperature adjustments were utilized

Reverse transcription 35 min; 50° C.

Tag activation 15 min; 95° C.

Cycle:

denaturation 30 s; 95° C.

annealing 60 s; 52° C.

extension 60 s; 72° C.

number of cycles 40

After the RT PCR, 4 µl of supernatant of the 50 µl reaction were applied to a 2% strength agarose gel and separated electrophoretically. After staining of the gel with ethidium bromide, a recording was made on a gel documentation device.

Figure 6:
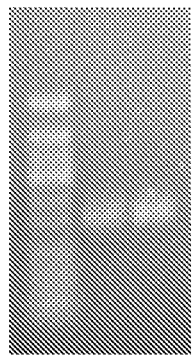
FIG. 6 shows the agarose gel depicting specific bands (middle and right trace) having the expected size (202 bp) confirming the detection of the RNA for both samples of the fr-phages.

FIG. 6 shows on the agarose gel (2% strength) that both samples of the fr-phages isolation exhibit a specific band (middle and right trace) having the expected size (202 bp). Thus this amplification based on RNA as starting material can be rated as successful. A single RT-PCR can successfully detect $5 \times 10^6$ PFU of phage fr after the RNA preparation and amplification. The left trace shows the DNA lengths standard)

This and the sixth exemplary embodiment clearly show that the process according to the invention can be employed for the purification (isolation) and amplification of nucleic acids (as described in detail above), in addition to the isolation and amplification of DNA, just as well for the isolation and amplification of RNA. We refer to the above disclosure.

In the course of a sixth exemplary embodiment, HeLa cells were employed for the isolation of RNA.

The following materials were employed:

Cultured HeLa cells (human cervical carcinoma cell line).

The cells were cultured in cell culture flasks by means of standard cell culture protocols. After washing with PBS, the cells were trypsinized and the cell count was determined under the microscope.

AX1 anion exchange beads lysis buffer GE (01% PVP MW 10,000; 0.45% Tween-20; 0.45% NP 40; 10 mM tris/Cl pH 7.5; 1 mM EDTA)

The procedure was according to the following protocol:

500 µl of $10^5$, or $10^3$ Hela cells in PBS are mixed with 1 ml of buffer GE, 20 µl of proteinase K and 20 µl of AX1 MagBeads in a 2.2 ml microtube Incubation: 15 min on an Eppendorf thermomixer at 56° C. and 1400 rpm magnetic separation and discarding of the supernatant wash Mag Beads 2× with buffer GE (800 µl each; vortex briefly; magnetic separation and discarding of the residue)

resuspend MagBead sediment in 100 µl of double-distilled water and transfer to a PCR tube carefully and quantitatively remove supernatant resuspend beads using 50 µl of RT-qPCR solution and start PCR in a real-time cycler For the RT-qPCR, the following temperature adjustments were utilized 25 µl of 2× QuantiTect sample RT-PCR Master Mix 0.5 µl of Fwd primer (human lamin A; GGCGGGTG-GATGCTGAGAACA (SEQ ID NO: 13): 10 µM)

0.5 µl of Rev primer (human lamin A; TGTCAATCTC-CACCAGTCGGG (SEQ ID NO: 14): 10 µM)

0.25 µl of sample (human lamin A; ATCTACAGTGAG-GAGCTGCGTGAGA (SEQ ID NO: 15) (5'-Fam; 3'-BHQ1; 10 µM)

0.5 µl of RT mix 23.25 µl of water

For the RT-PCR, the following temperature adjustments were utilized

Reverse transcription 30 min; 50° C.
Taq activation 15 min; 95° C.
Cycle:
denaturation 15 s; 94° C.
annealing/extension 60 s; 60° C.
number of cycles: 40

Figure 7:
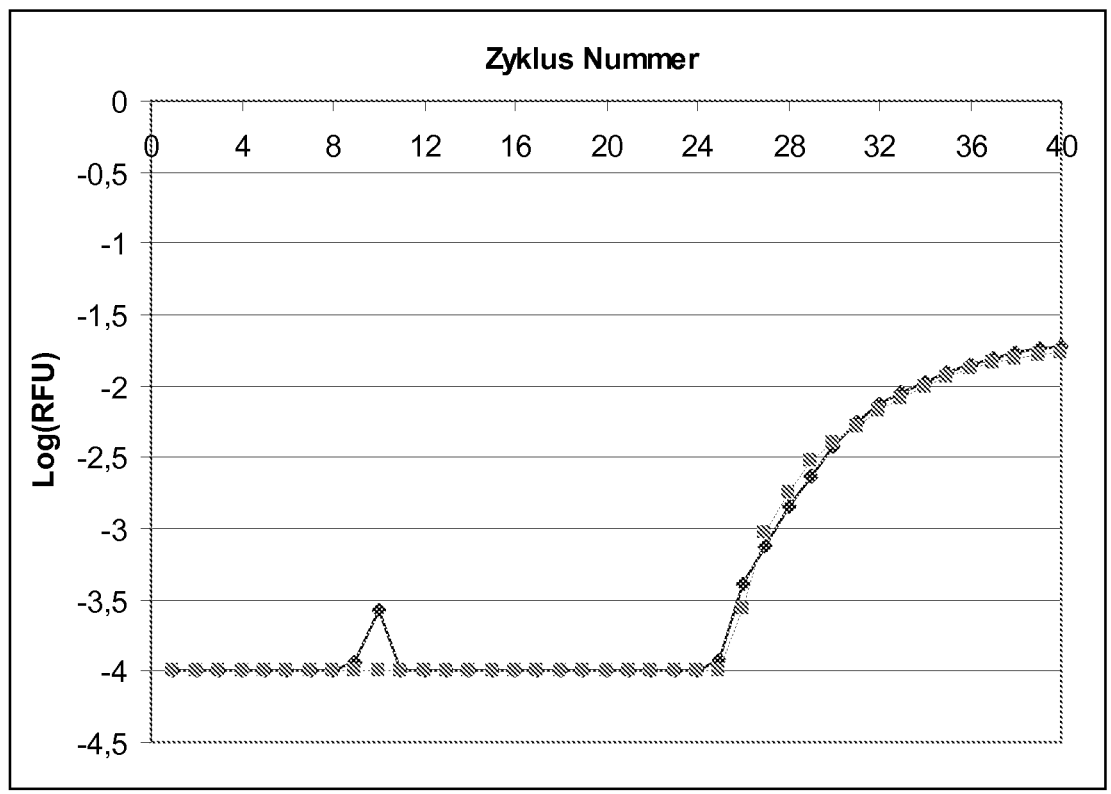
FIG. 7 shows an "amplification plot" of a real-time PCR of RNA isolated from HeLa cells.

FIG. 7 shows an "amplification plot" of a real-time PCR. The curve shows the increase in the fluorescence of two RT QPCR amplifications of HeLa RNA preparations as a function of the number of the PCR cycle and thus clear amplification signals that prove that, using the process described, RNA was isolated from HeLa cells, since the primer/sample sequences of the amplified lamin A gene are chosen such that because of exon/intron structures of the gene, an amplification can start only starting from a spliced RNA. The example moreover also shows that under certain circumstances a second amplification can also be dispensed with.

Figure 5:
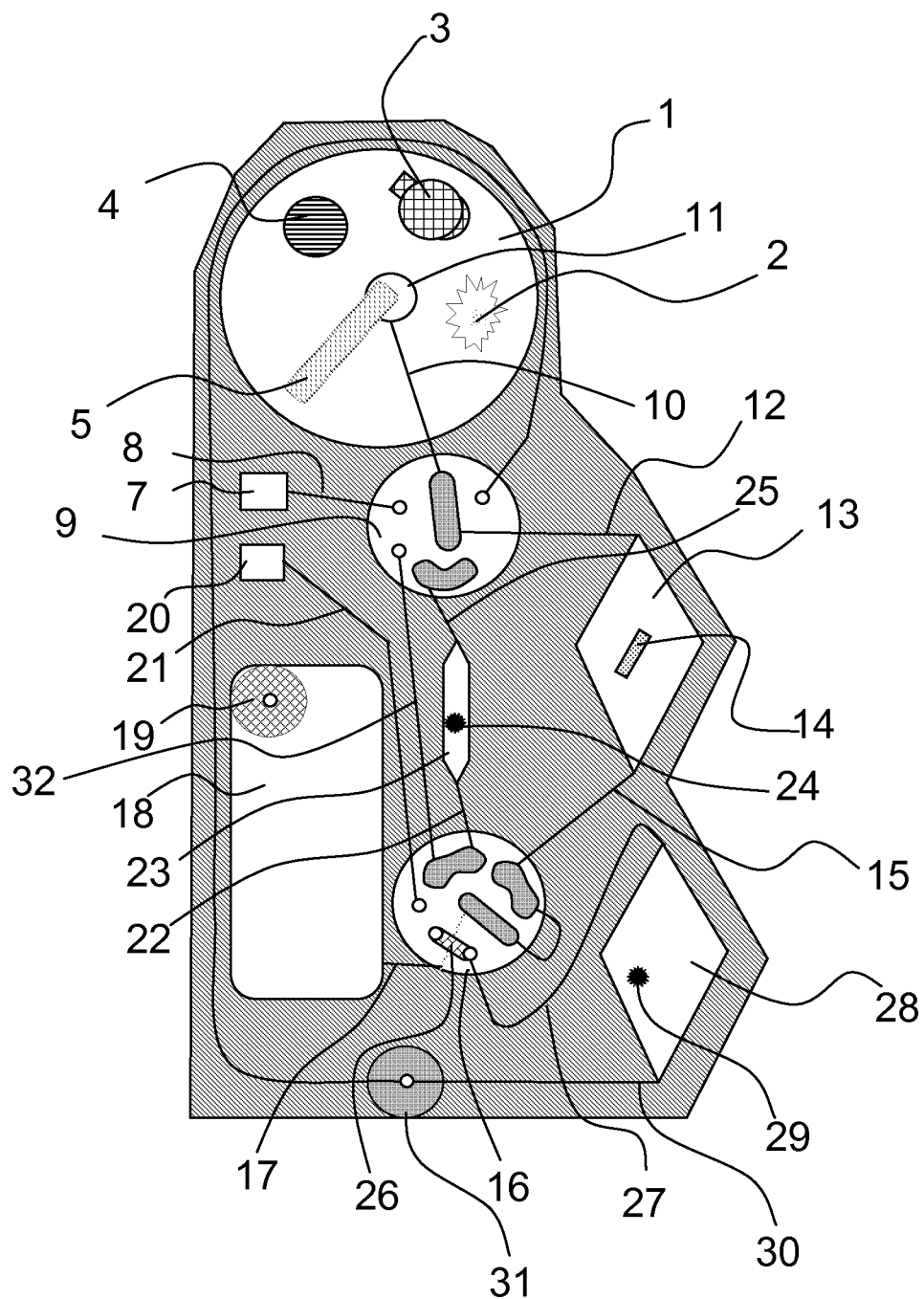
FIG. 5 provides an example of a closed system in accordance with one aspect of the invention.

The process can easily be performed in a closed system in order thus to avoid contamination. In FIG. 5, an example of a closed system for performing the process is shown in section. The device shown comprises a lysis chamber 1, in which magnetic beads (in addition to proteinase K) 2 for the binding of nucleic acid are already located. The lysis chamber 1 has a sealable opening 3, by means of which a biological sample is introduced into the lysis chamber 1. The lysis chamber 1 is provided with a pressure equalization valve 4 in order to be able to regulate the pressure prevailing in the lysis chamber 1, or to empty this if required by means of overpressure. In the lysis chamber is situated a rod-shaped magnet 5, with which the lysis can be mechanically assisted. If the magnet rotates rapidly enough, the magnetic beads separate with the bound nucleic acids and can be conducted further. Particularly simply, however, the lysis can also be assisted mechanically in this case with the aid of ultrasound.

In the lysis chamber 1, the sample is digested by pumping a lysis buffer into the lysis chamber via a connection 7, a channel 8, a valve unit 9, and a channel 10 from below via an opening 11. The sample digested enzymatically by the lysis buffer and with stirring binds to the magnetic beads by anion exchange. After binding, the lysis buffer together with the magnetic beads and the nucleic acids bound thereto are aspirated through the opening 11 and pumped through the channel 10 to the valve unit 9 and from here led out via a channel 12 into a first PCR chamber 13. In the first PCR chamber 13 is situated a small permanent magnet 14, to which the magnetic beads 2 adhere. The lysis buffer is led further through a channel 15, a valve unit 16 and a channel 17 into a waste chamber 18. The waste chamber 18 has an outwardly leading opening 19 in order thus to avoid the formation of an overpressure in the waste chamber 18. The connection 19 can be a valve or in the simplest embodiment a semipermeable membrane (e.g. GoreTex™).

Via the connection 7, wash buffers are now introduced through the channel 8, the valve unit 9 and the channel 12 into the first PCR chamber and led further via the channel 15, the valve unit 16 and the channel 17 into the waste chamber 18 in order thus to wash the magnetic beads with the nucleic acids bound thereto. Finally, the further supply of wash buffers is stopped and the wash buffers are pumped out of the first PCR chamber. Water is now introduced into the system via a connection 20. The water passes through a channel 21 into the valve unit 16 and is introduced from this into a reagent chamber 23 via a channel 22. In the reagent chamber are situated dried reagents 24 in order to carry out a first PCR. The reagents 24 dissolve in the water and pass through a channel 25, the valve unit 9 and the channel 12 into the first PCR chamber 13. Here, a first, relatively unspecific amplification of nucleic acid is performed. After the amplification in the first PCR chamber 13, an aliquot of the PCR reaction solution is introduced via the channel 15 into a measuring channel 26 of the valve unit 16 further via channel 17 into the waste chamber 18. The valve unit 16 is now shut such that water can be introduced via a connection 20, and is led via the channel 21 and the valve unit 16 and the measuring channel 26 with the specified volume of PCR reaction solution containing the amplified nucleic acid strands situated therein, directly further via a channel 27, to a second PCR chamber 28.

In the second PCR chamber 28 are situated reagents 29 for performing a second PCR, in which the amplification is very specific. The second PCR chamber 28 is connected to a channel 30, which externally comprises a connection 31, which can be present in the form of a valve. By means of the connection 31, a pressure equalization is made possible in the second PCR chamber 28.

The device shown in FIG. 5 comprises a channel 32 that connects the two valve units 9 and 16 to one another. This channel 32 is needed for the resuspension of the dried reagents in the chamber 23. For the resuspension, water flows via the access 20 and the channel 21 into the valve unit 16 and is then led through the channel 32 into the valve unit 9. From there, the water flows further through the stations 25, 23 and 22 to the valve unit 16 and then further through the channel 15 to the first PCR chamber 13, which is thus filled from below. Deaeration of the chamber takes place via the stations 12 and 9 and the channel 30 via the element 31.

The device shown in FIG. 5 can be designed as a disposable article, since this can be manufactured from inexpensive materials and in small form. For performing the process, this device is employed in a further device that provides for an automated performance of the process. The further device then actuates and controls the valve units (9, 16) automatically, and also the supply of buffers and water.

The specific amplification in the second PCR chamber can be detected by means of real-time fluorescence detection or by high-resolution DNA melt curve analysis. For both types of detection, an optical device for fluorescence detection is integrated into the second PCR chamber 28.

The invention claimed is:

1. A process for the preparation of a biological sample in a closed system comprising a lysis chamber fluidly connected to a first PCR chamber containing a restrained magnet inside the first PCR chamber, a second PCR chamber fluidly connected to the first PCR chamber, and a reagent chamber containing dried PCR reagents and fluidly connected to the first PCR chamber, the process comprising:
   a) digesting the biological sample in a lysis buffer in the lysis chamber;
   b) binding nucleic acids of the digested biological sample to magnetic particles in the lysis chamber;
   c) separating the magnetic particles having the bound nucleic acids from the lysis buffer;
   d) transferring the magnetic particles having the bound nucleic acids to the first PCR chamber;
   e) introducing water to the reagent chamber to dissolve the dried PCR reagents and transporting the dissolved reagents to the first PCR chamber;
   f) amplifying non-specifically the nucleic acids bound to the magnetic particles in a first PCR of a nested PCR in the first PCR chamber to produce unbound nucleic acid strands;
   g) separating the unbound nucleic acid strands in a supernatant from the nucleic acids bound to the magnetic particles with the restrained magnet disposed in the internal space of the first PCR chamber;
   h) transferring the supernatant to the second PCR chamber comprising PCR reagents; and
   i) amplifying specifically the unbound nucleic acid strands in a second PCR of the nested PCR in the second PCR chamber,
   wherein the lysis chamber, first PCR chamber, second PCR chamber and reagent chamber along with the fluidic connection between the lysis chamber and first PCR chamber, the fluidic connection between the first PCR chamber and reagent chamber, and the fluidic connection between the first PCR chamber and second PCR chamber, form a closed fluidic system; and wherein the restrained magnet is confined within the first PCR chamber.

2. The process as claimed in claim 1, wherein the bound nucleic acids are washed before the dissolved reagents are transported to the first PCR chamber in step f).

3. The process as claimed in claim 1, wherein the lysis buffer for the digesting has a salt content of in total less than 50 mM millimolar.

4. The process as claimed in claim 3, wherein the lysis buffer has a pH of 7.5 to 10.5, and the lysis buffer comprises tris, hepes or mops.

5. The process as claimed in claim 3, wherein the lysis buffer comprises nonionic detergents at 0.05% to 0.4% by volume.

6. The process as claimed in claim 3, wherein the lysis buffer comprises PVP up to 0.1% by volume.

7. The process as claimed in claim 1, wherein the digesting in step a) is performed with the aid of a magnetically driven stirring rod located inside the lysis chamber.

8. The process as claimed in claim 1, wherein the digesting in step a) is aided by ultrasound.

9. The process as claimed in claim 1, wherein the magnetic particles having the bound nucleic acids is separated from the lysis buffer with a magnet in step c).

10. The process as claimed in claim 1, wherein the magnetic particles having the bound nucleic acids are bound to the restrained magnet in the first PCR chamber before being amplified nonspecifically in step f).

11. The process as claimed in claim 1, wherein the supernatant is completely transferred to the second PCR chamber in step h).

12. The process as claimed in claim 1, wherein the supernatant is partially transferred to the second PCR chamber in step h).

13. The process as claimed in claim 1, wherein the supply and control of the buffer and water within the closed fluidic system is automated.

* * * * *